US012751694B2

(12) United States Patent
Izumi et al.

(10) Patent No.: US 12,751,694 B2
(45) Date of Patent: Oct. 6, 2026

(54) ULTRASONIC DIAGNOSTIC APPARATUS

(71) Applicant: CANON KABUSHIKI KAISHA, Tokyo (JP)

(72) Inventors: Minori Izumi, Shioyagunshioyamachi (JP); Taku Muramatsu, Otawara (JP); Tomoko Aizawa, Nasushiobara (JP); Katsuyuki Takamatsu, Yaita (JP); Takashi Koyakumaru, Utsunomiya (JP); Mitsuo Akiyama, Otawara (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 18/426,640

(22) Filed: Jan. 30, 2024

(65) Prior Publication Data

US 2024/0260933 A1 Aug. 8, 2024

(30) Foreign Application Priority Data

Feb. 3, 2023 (JP) ................................. 2023-015439

(51) Int. Cl.
*A61B 8/14* (2006.01)
*A61B 8/00* (2006.01)
*A61B 8/08* (2006.01)

(52) U.S. Cl.
CPC ............ *A61B 8/145* (2013.01); *A61B 8/0891* (2013.01); *A61B 8/4444* (2013.01); *A61B 8/466* (2013.01)

(58) Field of Classification Search
CPC ..... A61B 8/0891; A61B 5/0077; A61B 8/463; A61B 8/461
See application file for complete search history.

(56) References Cited

U.S. PATENT DOCUMENTS

2011/0144498 A1* 6/2011 Ando ..................... A61B 8/463 600/443
2012/0190981 A1* 7/2012 Harris ...................... A61B 5/14 604/95.01
2019/0380786 A1* 12/2019 Gran ...................... A61B 1/313
2021/0030486 A1* 2/2021 Zhang .................... A61B 34/20
2022/0104789 A1* 4/2022 Matsumoto .......... A61B 8/0891

FOREIGN PATENT DOCUMENTS

JP 2002-238898 A 8/2002

* cited by examiner

*Primary Examiner* — Amelie R Davis
(74) *Attorney, Agent, or Firm* — Oblon, McClelland, Maier & Neustadt, L.L.P.

(57) ABSTRACT

In one embodiment, an ultrasonic diagnostic apparatus includes: a display; a probe; and processing circuitry. The processing circuitry acquires an appearance image of an object that is scheduled to undergo dialysis, generates a 3D image from an echo signal acquired by the probe, the 3D image containing a plurality of frame images depicting inside of the object and positional information of each of the plurality of frame images, extracts a blood-vessel image depicting a blood vessel inside the object from the 3D image, generates a composite image of the appearance image and the blood-vessel image by aligning the appearance image and the blood-vessel image, and causes the display to display the composite image.

4 Claims, 15 Drawing Sheets

B-MODE DATA

COLOR DATA

COLOR DATA

COLOR DATA

CASE OF DETERMINATION EXPRESSION
(VESSEL DIAMETER * WEIGHTING COEFFICIENT A)
+ (1/ DEPTH FROM BODY SURFACE * WEIGHTING COEFFICIENT B)
+ (DISTANCE FROM OTHER BLOOD VESSEL * WEIGHTING COEFFICIENT C)

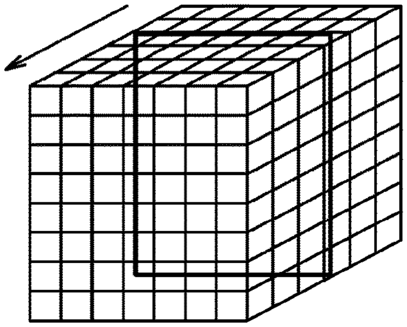

| WEIGHTING COEFFICIENT A | WEIGHTING COEFFICIENT B | WEIGHTING COEFFICIENT C |
|---|---|---|
| 10 | 5 | 1 |

| BLOOD VESSEL DIAMETER (mm) | DEPTH FROM BODY SURFACE (mm) | DISTANCE (mm) | DETERMINATION VALUE | RECOMMENDED ORDER |
|---|---|---|---|---|
| 12.0 | 13.0 | 20.0 | 140.4 | 1 |
| 9.7 | 22.0 | 30.0 | 127.2 | 2 |
| 7.6 | 7.0 | 25.0 | 101.7 | 3 |

FIG. 9A

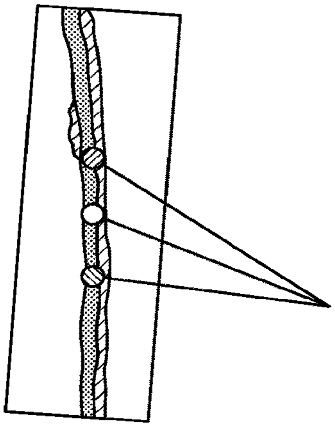

| | BLOOD VESSEL DIAMETER (mm) | DEPTH FROM BODY SURFACE (mm) | DISTANCE (mm) |
|---|---|---|---|
| ⊘ | 12.0 | 13.0 | 20.0 |
| ○ | 9.7 | 22.0 | 30.0 |
| ⊘ | 7.6 | 7.0 | 25.0 |

RECOMMENDED PUNCTURE POSITION

FIG. 9B

CREATION DATE AND TIME

VASCULAR ACCESS ECHO REPORT

ID ______ PATIENT NAME ______ DATE OF BIRTH:

ECO IMPLEMENTER ______ COMMENT INPUT PERSON ______ BLOOD TYPE:

| REASON | DIFFICULTY IN PUNCTURING, PROPOSED NEW BLOOD VESSEL, POOR BLOOD REMOVAL, FIRST PUNCTURE, OR OTHER REASONS (SOMETHING ABOUT SHUNT) | REASON | SHUNT (ARTERY/VEIN), ○○○ ○○○(○○○○), GRAFT, RED SHUNT |
|---|---|---|---|

POINTS TO BE NOTED IN CREATING REPORT

| DESCRIPTION ON INSTRUCTION | VA TROUBLE (PTA) HISTORY |
|---|---|
| | |

PATIENT INFORMATION

| ○○○ | | | |
|---|---|---|---|
| ○○ | | | |
| ○○ | | | |
| ○○ | | | |
| ○○ | | | |
| ○○○ | | | |

①

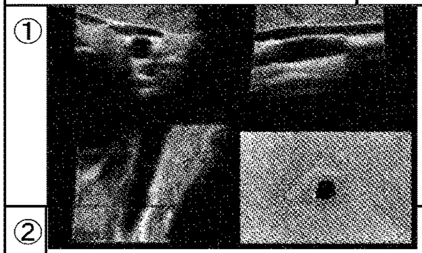

DISTANCE TO BLOOD VESSEL :
BLOOD VESSEL DIAMETER :

②

DISTANCE TO BLOOD VESSEL :
BLOOD VESSEL DIAMETER :

③

DISTANCE TO BLOOD VESSEL :
BLOOD VESSEL DIAMETER :

| CIRCULAR MARK | BLOOD VESSEL DIAMETER (mm) | DEPTH FROM BODY SURFACE (mm) | DISTANCE (mm) |
|---|---|---|---|
| (hatched circle) | 12.0 | 13.0 | 20.0 |
| ○ | 9.7 | 22.0 | 30.0 |
| (hatched circle) | 7.6 | 7.0 | 25.0 |

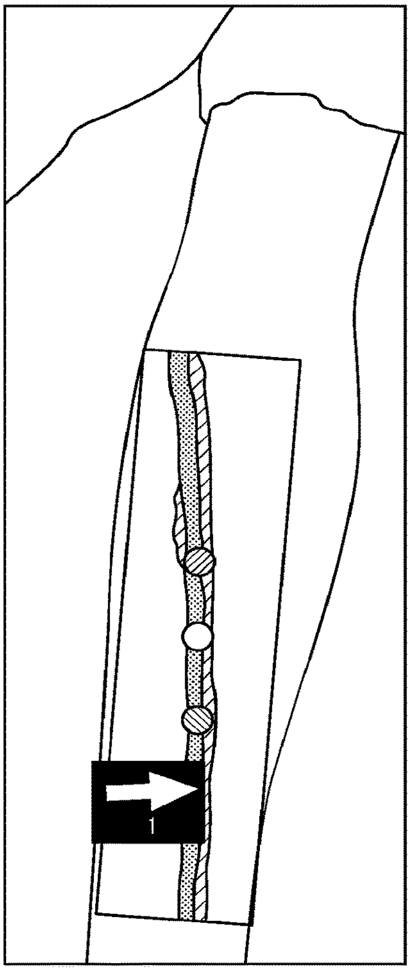

FIG. 14

ULTRASONIC DIAGNOSTIC APPARATUS

CROSS-REFERENCE TO RELATED APPLICATION

This application is based upon and claims the benefit of priority from Japanese Patent Application No. 2023-015439, filed on Feb. 3, 2023, the entire contents of which are incorporated herein by reference.

FIELD

Disclosed embodiments relate to an ultrasonic diagnostic apparatus.

BACKGROUND

During dialysis, an ultrasonic examination is performed on blood vessels of an object, and a schema report is created for the purpose of VA (Vascular Access) management and support for puncture. The report includes detailed information such as a schema shows mapping of the distribution of the blood vessel, depth of the blood vessel, blood-vessel diameter, information on the inside of the blood vessel wall, and information on edema and inflammation around the blood vessel. These information contribute to accurate puncture.

The schema report needs to contain a lot of information about blood vessels and is repeatedly used for observation over time, so accurate mapping is required in creating the schema report. Thus, there is a problem that it takes a long time to create a schema report.

BRIEF DESCRIPTION OF THE DRAWINGS

FIG. 9A is still another diagram illustrating the method for calculating the blood vessel parameters according to the first embodiment.

FIG. 9B is still another diagram illustrating the method for calculating the blood vessel parameters according to the first embodiment.

FIG. 14 is a diagram illustrating a schema report screen according to the first embodiment.

DETAILED DESCRIPTION

Hereinbelow, embodiments of an ultrasonic diagnostic apparatus will be described in detail by referring to the accompanying drawings.

In one embodiment, an ultrasonic diagnostic apparatus includes: a display; a probe; and processing circuitry. The processing circuitry acquires an appearance image of an object that is scheduled to undergo dialysis, generates a 3D image from an echo signal acquired by the probe, the 3D image containing a plurality of frame images depicting inside of the object and positional information of each of the plurality of frame images, extracts a blood-vessel image depicting a blood vessel inside the object from the 3D image, generates a composite image of the appearance image and the blood-vessel image by aligning the appearance image and the blood-vessel image, and causes the display to display the composite image.

First Embodiment

Figure 1:
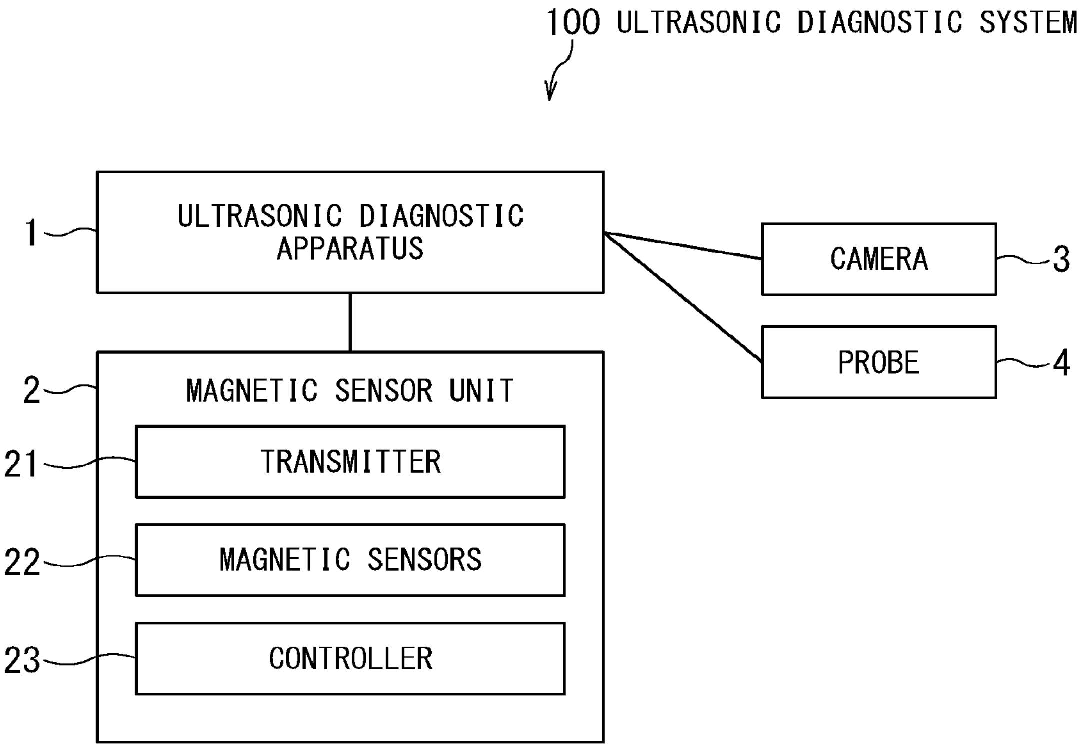
FIG. 1 is a block diagram illustrating a configuration of an ultrasonic diagnostic system according to the first embodiment.

The first embodiment relates to a configuration of an ultrasonic diagnostic apparatus 1 and processing to be executed by the ultrasonic diagnostic apparatus 1. FIG. 1 is a block diagram illustrating a configuration of an ultrasonic diagnostic system 100 according to the first embodiment.

The ultrasonic diagnostic system 100 includes the ultrasonic diagnostic apparatus 1, a magnetic sensor unit 2, a camera 3, and a probe (i.e., ultrasonic probe) 4. The ultrasonic diagnostic apparatus 1 receives positional information of the camera 3 and the probe 4 from the magnetic sensor unit 2, receives an optical image of an object from the camera 3, receives an echo signal inside the object from the probe 4, generates image data related to the object from the positional information, the optical image, and the echo signals, and displays the image data as an image on the display 10.

The magnetic sensor unit 2 can acquire the relative position of its magnetic sensors 22 with respect to the transmitter 21 by using magnetism. The camera 3 images the probe 4 configured to scan the object, and sends the generated image data to the ultrasonic diagnostic apparatus 1. In response to an instruction received from the ultrasonic diagnostic apparatus 1, the probe 4 generates and transmits an ultrasonic wave to the object, receives the ultrasonic wave (echo) reflected from the inside of the object's body, and sends an echo signal based on the echo to the ultrasonic diagnostic apparatus 1.

As shown in FIG. 1, the magnetic sensor unit 2 includes a transmitter 21, the magnetic sensors 22, and a controller 23. The transmitter 21 generates a magnetic field around itself by generating magnetism. The magnetic sensors 22 are respectively installed on the camera 3 and the probe 4. Each magnetic sensor 22 detects the magnitude and direction of the magnetic field generated by the transmitter 21, and sends information on the magnitude and direction of the magnetic field to the controller 23.

The controller 23 receives information on the magnitude and direction of the detected magnetic field from the respective magnetic sensors 22 installed on the camera 3 and the probe 4, and calculates the relative positions of the respective magnetic sensors 22 with respect to the transmitter 21 (for example, three-dimensional coordinates in which the position of the transmitter 21 is the origin) based on the magnitude and direction of the magnetic field. Further, the controller 23 transmits the relative positions of the respective magnetic sensors 22 to the ultrasonic diagnostic apparatus 1 as positional information of each of the camera 3 and the probe 4. For example, regarding the magnetic sensors 22 within a range of about 1 meter from the transmitter 21, the distance and direction from the transmitter 21 can be measured.

Figure 2:
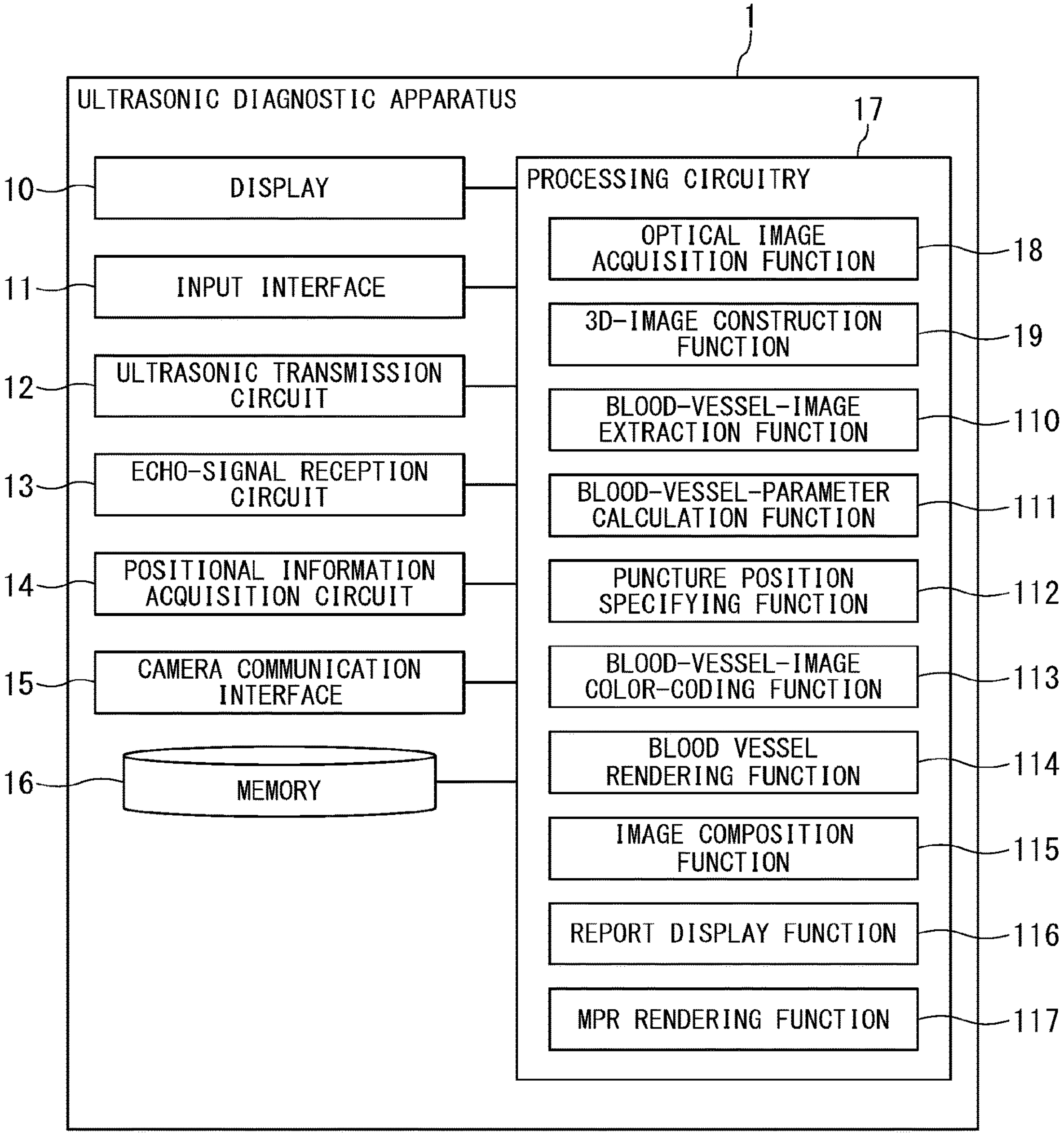
FIG. 2 is a block diagram illustrating a configuration of an ultrasonic diagnostic apparatus according to the first embodiment.

FIG. 2 is a block diagram illustrating the configuration of the ultrasonic diagnostic apparatus 1 according to the first embodiment. As shown in FIG. 2, the ultrasonic diagnostic apparatus 1 includes a display 10, an input interface 11, an ultrasonic transmission circuit 12, an echo-signal reception circuit 13, a positional information acquisition circuit 14, a camera communication interface 15, a memory 16, and processing circuitry 17. This processing circuitry 17 includes an optical image acquisition function 18, a 3D-image construction function 19, a blood-vessel-image extraction function 110, a blood-vessel-parameter calculation function 111, a puncture-position specifying function 112, a blood-vessel-image color-coding function 113, a blood vessel rendering function 114, an image composition function 115, a report display function 116, and an MPR (Multi Planar Reconstruction) rendering function 117.

The display 10 is composed of a general display output device such as a liquid crystal display and an OLED (Organic Light Emitting Diode) display, for example. The input interface 11 receives user operations. The input interface 11 is, for example, an operation console that includes operation buttons. The input interface 11 includes an input circuit. The ultrasonic transmission circuit 12 outputs an instruction to transmit an ultrasonic wave to the connected probe 4. The probe 4 transmits an ultrasonic wave toward the object in response to this instruction, and receives the echo signal reflected within object. The echo-signal reception circuit 13 acquires the echo signal from the probe 4.

The positional information acquisition circuit 14 acquires positional information of each of the camera 3 and the probe 4 from the magnetic sensor unit 2 connected to the ultrasonic diagnostic apparatus 1. The camera communication interface 15 transmits an imaging instruction to the camera 3, which is connected to the ultrasonic diagnostic apparatus 1 via a connection tool such as a USB, and receives the generated image data from the camera 3. The camera communication interface 15 includes a communication circuit.

The memory 16 stores data and reads in the stored data in response to an instruction from the processing circuitry 17. The memory 16 is a storage device such as an HDD (Hard Disk Drive) and an SSD (Solid State Drive).

The processing circuitry 17 controls the entirety of the ultrasonic diagnostic apparatus 1. The processing circuitry 17 is a processor that generates and displays each image by reading out and executing programs stored in the memory 16.

The processing circuitry 17 implements each of the functions 18, 19, and 110 to 117 by executing the programs.

The optical image acquisition function 18 includes a function to acquire an optical image of the arm (external appearance) of the object to be subjected to dialysis. The optical image is an example of an appearance image.

The 3D-image construction function 19 includes a function to construct or acquire a 3D image, which contains a plurality of frame images depicting the inside of the object and positional information of each of the frame images, by using the positional information of the probe 4 and the ultrasonic image (echo signal) acquired from the probe 4. Note that each of the frame images is one frame of an ultrasonic image.

The blood-vessel-image extraction function 110 includes a function to extract a blood-vessel image indicative of branching and distribution of blood vessels inside the object from the 3D image.

The blood-vessel-parameter calculation function 111 uses the 3D image to calculate blood vessel parameters including blood-vessel diameter, vascular depth from the body surface, and distance to another blood vessel shown in the plurality of frame images. Each blood vessel parameter is an example of blood vessel data. The blood-vessel-parameter calculation function 111 also includes a function of using an existing technique for determining whether a blood vessel in the 3D image is an artery or a vein. For example, if the blood vessel has pulsations, the blood-vessel-parameter calculation function 111 determines this blood vessel to be an artery. If there is no pulsation, this blood vessel is determined to be a vein.

The puncture-position specifying function 112 includes a function to: (i) specify a recommended puncture position from blood vessels shown in the plurality of frame images on the basis of the blood vessel parameters; and (ii) put a mark indicative of the recommended puncture position in the blood-vessel image depicting inside of the object.

The recommended puncture position is the recommended position for puncturing a needle in dialysis.

The blood-vessel-image color-coding function 113 includes a function to color a blood-vessel image using a chromatic color or an achromatic color on the basis of: whether the blood vessel is an artery or a vein, the blood-vessel diameter, and the vascular depth from the body surface.

The blood vessel rendering function 114 includes a function to generate an image of a blood vessel portion from the 3D image.

The image composition function 115 includes a function to compose the optical image of the arm of the object and the image of the blood vessel portion rendered from the 3D image by aligning both images with each other.

The report display function 116 includes a function to display the composite image on a schema report screen of the display 10. The report display function 116 further includes a function to display the recommended puncture position specified by the puncture-position specifying function 112 on the schema report screen of the display 10.

The MPR rendering function 117 includes a function to generate cross-sectional images in three orthogonal directions of an arbitrary position in the 3D image.

Figure 3:
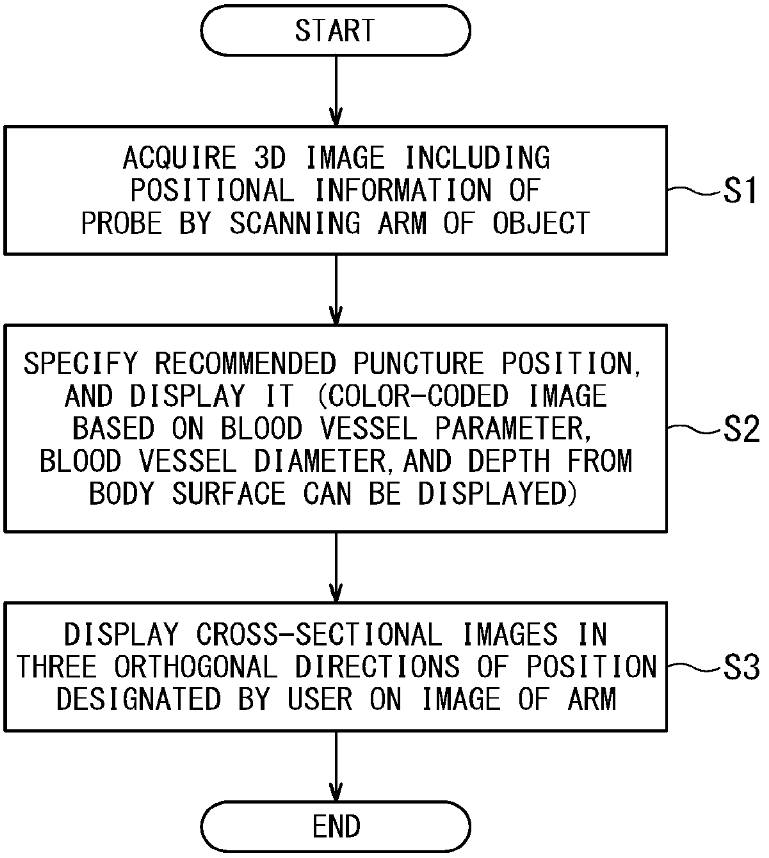
FIG. 3 is a flowchart illustrating an outline of the processing to be executed by the ultrasonic diagnostic apparatus according to the first embodiment.

FIG. 3 is a flowchart illustrating an outline of the processing to be executed by the ultrasonic diagnostic apparatus 1 according to the first embodiment.

In the step S1, as a result of a scan that is performed by a user on the arm of the object with the use of the probe 4 equipped with one magnetic sensor 22, the ultrasonic diagnostic apparatus 1 acquires a 3D image containing a plurality of frame images depicting the inside of the arm and positional information of each frame image.

In the step S2, the ultrasonic diagnostic apparatus 1 extracts a blood-vessel image showing a blood vessel from the 3D image, specifies the recommended puncture position, and displays the recommended puncture position on the schema report screen on the display 10. The ultrasonic diagnostic apparatus 1 may cause the display 10 to display blood vessel parameters including blood-vessel diameter, vascular depth from the body surface, and distance from another blood vessel. Further, the ultrasonic diagnostic apparatus 1 may cause the display 10 to display a blood-vessel image that is color-coded depending on whether the blood vessel is an artery or vein, the blood-vessel diameter, and the vascular depth from the body surface.

In the step S3, the ultrasonic diagnostic apparatus 1 causes the display 10 to display cross-sectional images in three orthogonal directions of the position designated by the user with the cursor on the optical image of the arm of the object.

Figure 4:
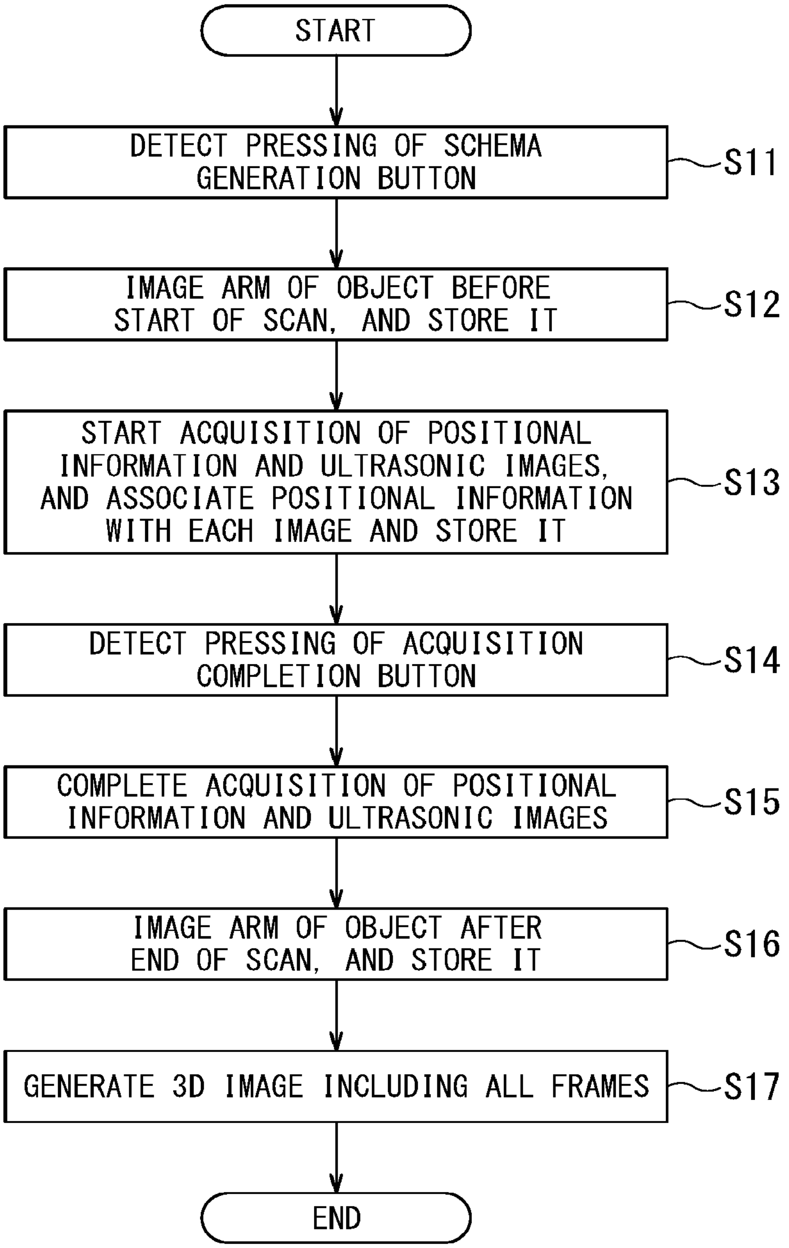
FIG. 4 is a flowchart illustrating details of the processing of acquiring a 3D (three-dimensional) image in the step S1.
Figure 5A:
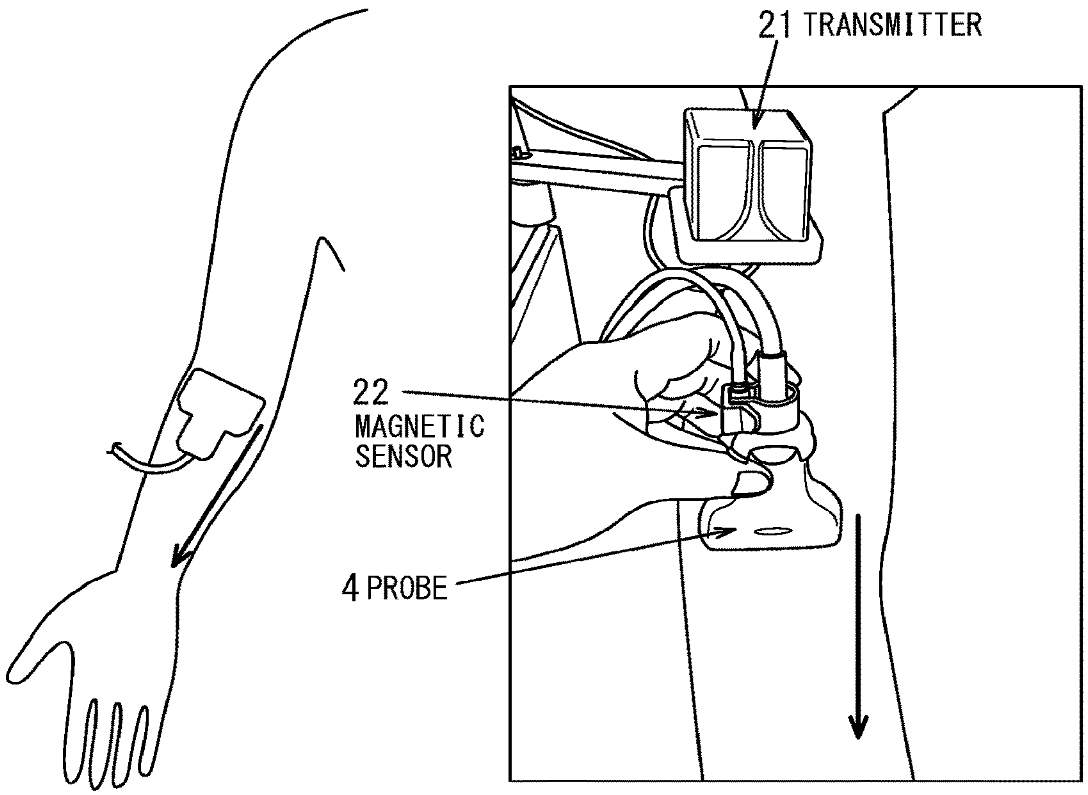
FIG. 5A is a diagram illustrating disposition of a magnetic sensor unit, a camera, and a probe according to the first embodiment.
Figure 5B:
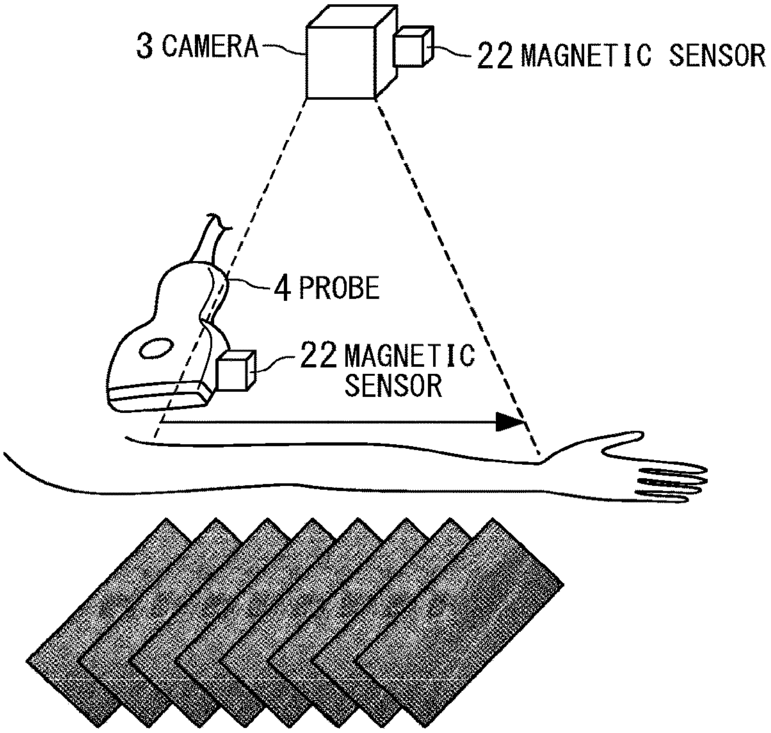
FIG. 5B is another diagram illustrating the disposition of the magnetic sensor unit, the camera, and the probe according to the first embodiment.

FIG. 4 is a flowchart illustrating details of the processing of acquiring the 3D image in the step S1. FIG. 5A and FIG. 5B are diagrams illustrating disposition of the magnetic sensor unit 2, the camera 3, and the probe 4 according to the first embodiment.

As shown in FIG. 5A and FIG. 5B, the camera 3 is disposed vertically above the object's arm, and one magnetic sensor 22 is installed on the camera 3. The other magnetic sensor 22 is installed on the probe 4. The user places the probe 4 at the scanning start position of the arm of the object. Subsequently, the user presses a schema creation button on the input interface 11 of the ultrasonic diagnostic apparatus 1.

In response to pressing of the schema creation button, the processing circuitry 17 of the ultrasonic diagnostic apparatus 1 starts processing. The details of this processing are described below on the basis of FIG. 4.

In the step S11, the processing circuitry 17 receives a signal indicating pressing of the schema creation button from the input interface 11. In response to reception of this signal, the processing circuitry 17 detects that the schema creation button is pressed, and performs the processing of the steps S12 and S13.

In the step S12, the optical image acquisition function 18 of the processing circuitry 17 causes the camera communication interface 15 to transmit the imaging instruction to the camera 3. The camera 3 receives the imaging instruction from the camera communication interface 15, images the arm of the object before start of the scan, and transmits the optical image of the arm to the camera communication interface 15. The optical image acquisition function 18 of the processing circuitry 17 acquires the optical image received by the camera communication interface 15, and stores the optical image in the memory 16 as image data indicating the position of the probe 4 before start of the scan.

In the step S13, the processing circuitry 17 starts acquisition of positional information and ultrasonic images. First, the processing circuitry 17 acquires the positional information of each of the camera 3 and the probe 4 from the magnetic sensor unit 2 via the positional information acquisition circuit 14. During the same time period, the processing circuitry 17 outputs an ultrasonic transmission instruction to the probe 4 via the ultrasonic transmission circuit 12 and acquires an echo signal from the probe 4 via the echo-signal reception circuit 13. The processing circuitry 17 then associates the positional information of the probe 4 with the frame image based on the acquired echo signal and stores this frame image in the memory 16. The processing circuitry 17 performs the above-described processing for the plurality of frame images to be time-sequentially generated.

When the scan is completed, the user presses the acquisition completion button on the input interface 11 of the ultrasonic diagnostic apparatus 1.

In the step S14, the processing circuitry 17 receives a signal indicating pressing of the acquisition completion button from the input interface 11. As a result, the processing circuitry 17 detects that the acquisition completion button is pressed, and then executes the processing of the steps S15 and S16.

In the step S15, the processing circuitry 17 completes acquisition of the positional information and the ultrasonic images.

In the step S16, the optical image acquisition function 18 of the processing circuitry 17 causes the camera communication interface 15 to transmit the imaging instruction to the camera 3. The camera 3 receives the imaging instruction from the camera communication interface 15, images the arm of the object after the scan, and transmits the optical image of the arm to the camera communication interface 15. The optical image acquisition function 18 of the processing circuitry 17 acquires the optical image received by the camera communication interface 15, and stores the optical image in the memory 16 as the image data indicating the position of the probe 4 after the scan.

The reason to image the object before and after acquiring the positional information and the ultrasonic images using the camera 3 is to detect the probe 4 depicted in the optical image and use the position of the probe 4 for aligning the 3D image constructed from the ultrasonic images with the optical image.

In the step S17, the processing circuitry 17 reads out the acquired positional information and the ultrasonic images of the probe 4 from the memory 16. The 3D-image construction function 19 of the processing circuitry 17 constructs a 3D image in a voxel format. The positional information acquired from the magnetic sensor unit 2 includes the position of each magnetic sensor 22 (X, Y, Z) and the tilt angle (i.e., inclination) of each magnetic sensor 22 (θx, θy, θz). The position of each magnetic sensor 22 is, for example, the relative position of the magnetic sensor 22 with respect to the transmitter 21. The tilt angle of each magnetic sensor 22 is, for example, the rotation angle of the magnetic sensor 22 with respect to the reference axis of the transmitter 21. The 3D-image construction function 19 constructs the 3D image that includes the ultrasonic images of all the frames from the positional information associated with the ultrasonic images of the respective frames.

Figure 6:
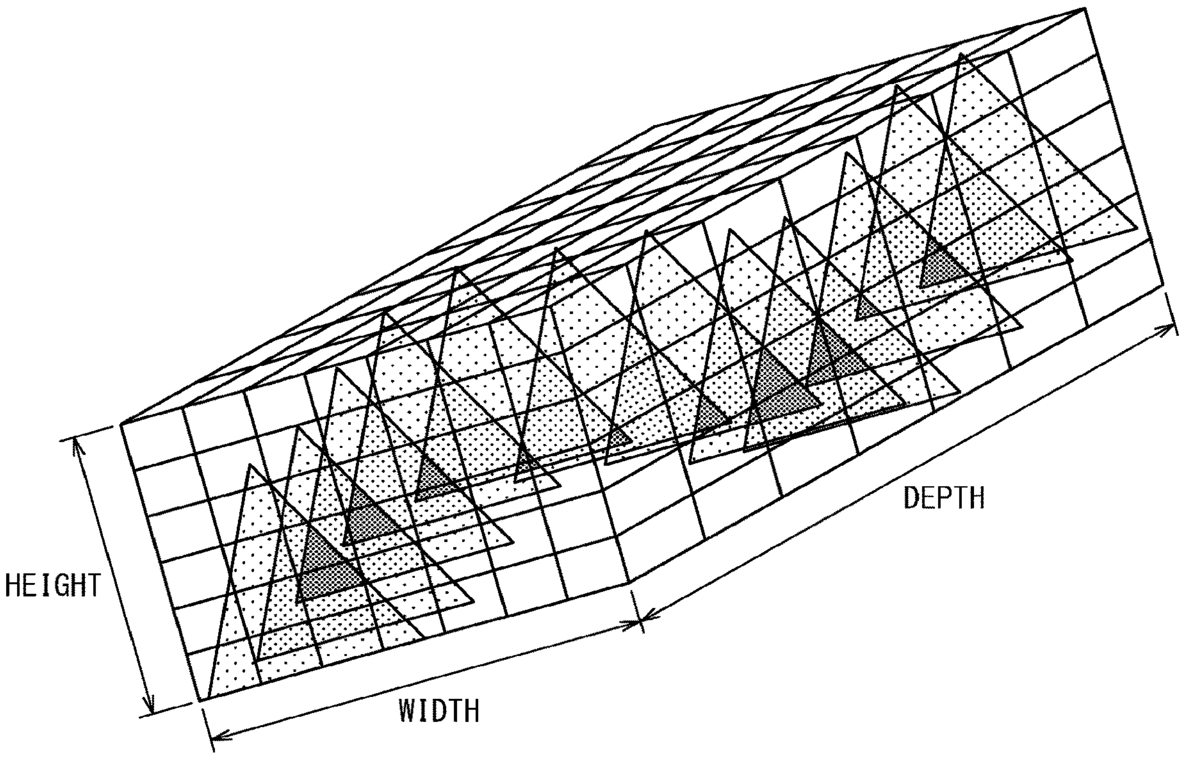
FIG. 6 is a diagram illustrating a 3D image according to the first embodiment.

FIG. 6 illustrates the 3D image according to the first embodiment. Each triangle shown in FIG. 6 is an example of a frame image. For example, ten frame images are time-sequentially acquired per second. The 3D-image construction function 19 sets a rectangular parallelepiped including all the acquired frame images as the 3D image. In detail, the height of the rectangular parallelepiped corresponds to the difference between the highest point and the lowest point of the height of the frame images. The width of the rectangular parallelepiped corresponds to the difference between the rightmost point and the leftmost point of the width of the frame images. The depth of the rectangular parallelepiped corresponds to the number of the frame images. As shown in FIG. 6, the rectangular parallelepiped is an aggregation or collection of small cubes (regular lattice units).

Figure 7:
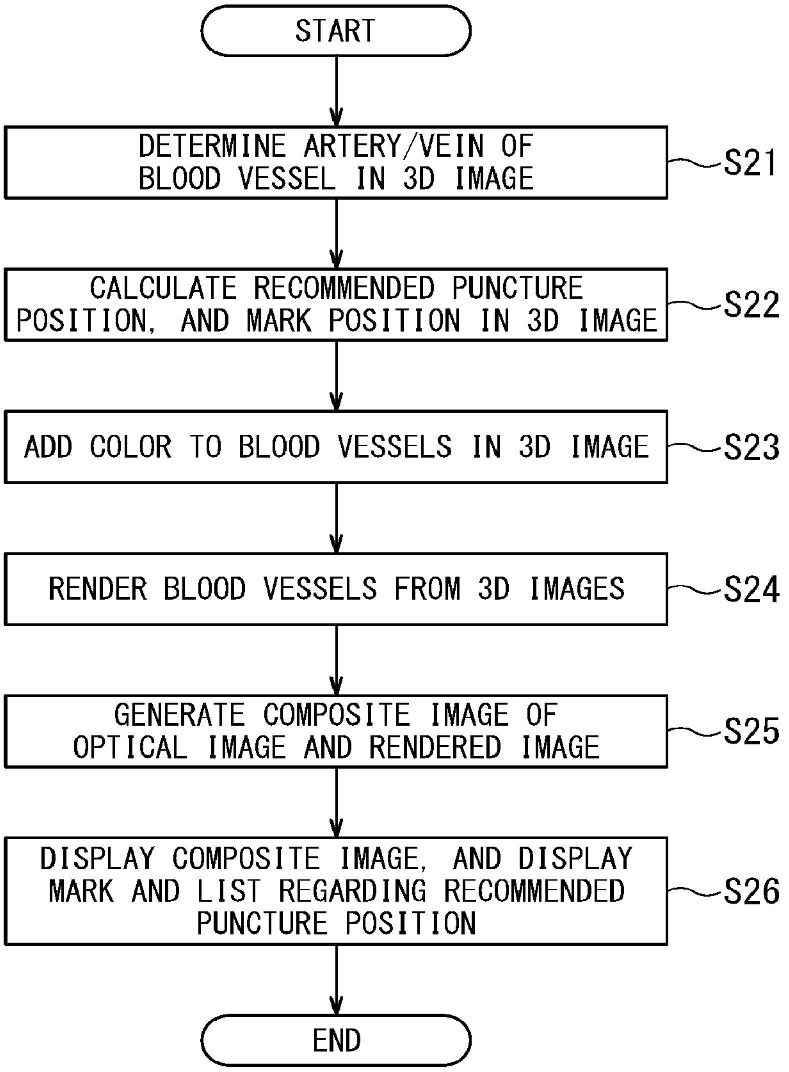
FIG. 7 is a flowchart illustrating details of processing of calculating and displaying a recommended puncture position in the step S2.

FIG. 7 is a flowchart illustrating details of the processing of extracting the blood vessel image and calculating and displaying the recommended puncture position in the step S2 of FIG. 3.

In the step S21, the blood-vessel-image extraction function 110 of the processing circuitry 17 extracts the blood vessel portion (blood-vessel image) from the 3D image. The blood-vessel-image extraction function 110 acquires color data indicating the state of the blood flow as the blood vessel portion, for example. Further, the blood-vessel-parameter calculation function 111 determines whether each blood vessel included in the extracted blood vessel portion is an artery or a vein. Since the puncture is performed on a vein, the location of the vein must be specified.

In the step S22, the blood-vessel-parameter calculation function 111 of the processing circuitry 17 calculates the depth of the vein, the diameter of the vein, and the distance between the vein and another blood vessel in each frame image included in the voxel-format 3D image. Further, the puncture-position specifying function 112 specifies the recommended puncture position on the basis of these values (blood-vessel parameters), and puts a mark indicating the recommended puncture position on the blood vessel portion in the 3D image. The details are described below.

Figure 8A:
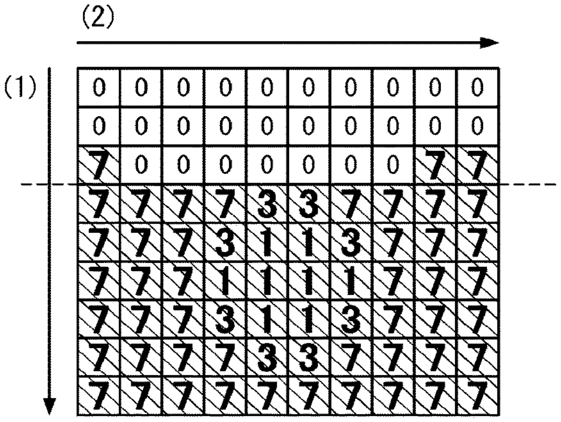
FIG. 8A is a diagram illustrating a method for calculating blood vessel parameters according to the first embodiment.
Figure 8B:
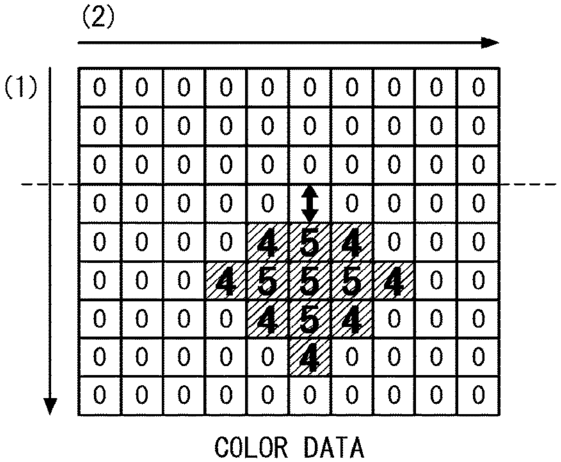
FIG. 8B is another diagram illustrating the method for calculating the blood vessel parameters according to the first embodiment.

FIG. 8A to FIG. 8D and FIG. 9A and FIG. 9B illustrate the method for calculating the blood vessel parameters according to the first embodiment. FIG. 8A and FIG. 8B illustrate examples of how to calculate the depth of each blood vessel from the skin surface or body surface of the arm (i.e., vascular depth from the body surface). The ultrasonic images include B-mode data (B-mode images) indicating the state of tissues and color data indicating the state of the blood flow. The B-mode data and the color data can be acquired at the same time.

FIG. 8A illustrates the case of the B-mode data. The B-mode data are used to specify the position of the body surface. Among the values of the B-mode data, 0 is defined as no ultrasonic data (i.e., a value outside the FOV or Field of View), and any value excluding 0 is defined as the amplitude intensity of the echo signal. In other words, the outside and inside of the FOV are distinguished by 0 and nonzero values. As shown in FIG. 8A, the blood-vessel-parameter calculation function 111 scans each column of the B-mode data from the top (i.e., first row) in the depth direction (1), and treats the boundary between 0 and nonzero value region (a region having echo signals) as the body surface.

FIG. 8B illustrates the case of the color data. The color data are used to specify the position of the blood vessel and determine the depth of the blood vessel from the body surface. Among each value of the color data, 0 is defined as no color Doppler data, and any nonzero value is defined as the intensity of the color signal. As shown in FIG. 8B, the blood-vessel-parameter calculation function 111 scans each column of the color data from the top (i.e., first row) in the depth direction (1), and treats an aggregation of color signals (i.e., region where colored pixels are continuous) being larger than a threshold value (i.e., noise signal) as a blood vessel. The blood-vessel-parameter calculation function 111 calculates the depth of the blood vessel on the basis of both the pixel size (i.e., actual size of one pixel) and the distance (number of pixels) from the pixel of the body surface, as detected from the B-mode data, to the color data.

Figure 8C:
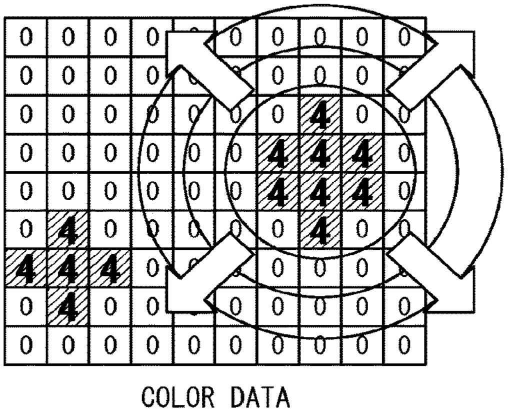
FIG. 8C is still another diagram illustrating the method for calculating the blood vessel parameters according to the first embodiment.

FIG. 8C illustrates an example of how to calculate the distance between blood vessels in the case of the color data. As shown in FIG. 8C, the blood-vessel-parameter calculation function 111 scans the 3D image data radially in all the three-dimensional directions from a specific blood vessel until reaching another blood vessel. Among all the distances between any pixel constituting this specific blood vessel and any pixel constituting another blood vessel being reached, the shortest distance is treated as the distance between both blood vessels.

When there is only one blood vessel in the frame image and no other blood vessels, the blood-vessel-parameter calculation function 111 sets the distance between the blood vessels to 0. When a plurality of blood vessels are depicted in the frame image, the blood-vessel-parameter calculation function 111 treats the shortest distance as defined above as the distance between blood vessels.

Figure 8D:
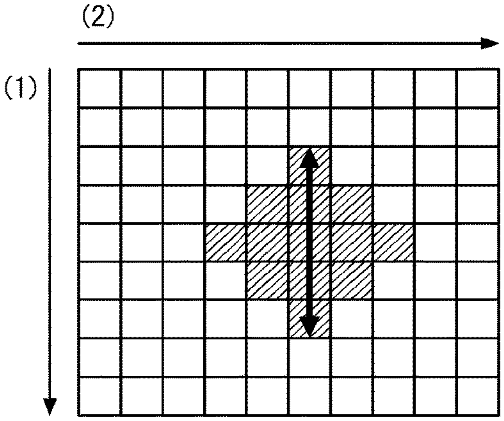
FIG. 8D is still another diagram illustrating the method for calculating the blood vessel parameters according to the first embodiment.

FIG. 8D illustrates an example of how to calculate the blood-vessel diameter in the case of the color data. As the blood-vessel diameter, the diameter in the depth direction (1) (i.e., direction perpendicular to the body surface) is calculated. The blood-vessel-parameter calculation function 111 scans an aggregation of color signals in the depth direction (1) from the top (i.e., first row) of each column in the color data, and treats the longest distance between the top end and the bottom end of the aggregation in the depth direction (1) as the blood-vessel diameter.

FIG. 9A and FIG. 9B illustrate a method for specifying the recommended puncture position. As shown in FIG. 9A, the puncture-position specifying function 112 calculates a determination value for each blood vessel in each frame by using the blood vessel parameters and the calculation formula shown in Expression 1.

$$\text{Determination Value} = \text{Vessel Diameter (mm)} * \text{Weighting Coefficient } A + 1/(\text{Depth from Body Surface (mm)} * \text{Weighting Coefficient } B) + (\text{Distance from Other Blood Vessel (mm)} * \text{Weighting Coefficient } C) \quad \text{Expression 1}$$

The puncture-position specifying function 112 specifies the top three determination values in descending order among the calculated values.

As shown in FIG. 9B, the puncture-position specifying function 112 puts a circular mark indicative of the recommended puncture position corresponding to the determination value on the blood vessel portion of the 3D image. Note that the coloring of the circular mark is performed in the step S24.

Figure 10A:
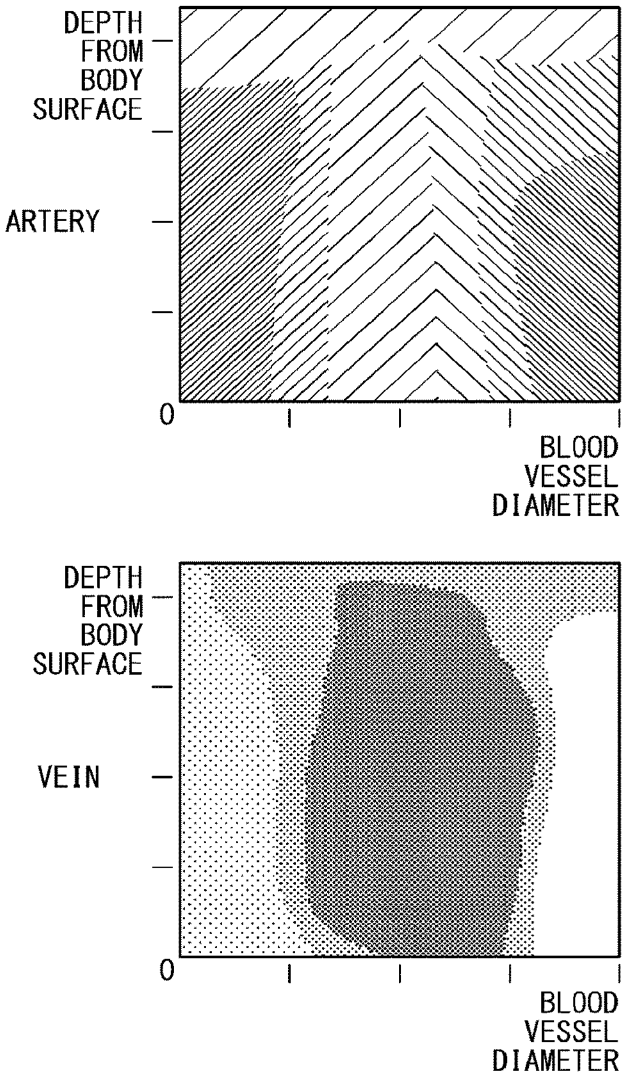
FIG. 10A is a diagram illustrating color-coding of blood vessels according to the first embodiment.
Figure 10B:
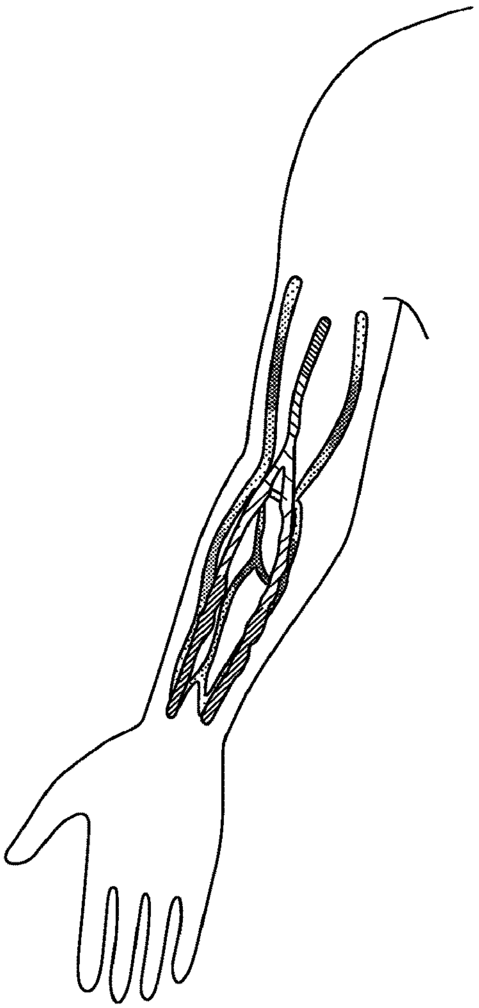
FIG. 10B is another diagram illustrating the color-coding of blood vessels according to the first embodiment.

In the step S23, the blood-vessel-image color-coding function 113 color-codes the blood-vessel portion depicted in the 3D image according to: blood-vessel diameter, vascular depth from the body surface, and whether the blood vessel is an artery or a vein. FIG. 10A and FIG. 10B illustrate the color-coding of blood vessels according to the first embodiment. As shown in FIG. 10A, the blood-vessel-image color-coding function 113 distinguishably determines the respective colors of the blood vessels according to their blood-vessel diameter, vascular depth from the body surface, and whether they are arteries or veins. As shown in FIG. 10B, the blood-vessel-image color-coding function 113 performs color-coding for each portion of the blood vessels. The colors assigned for the respective blood vessel portions in the blood-vessel image enables the user to distinguish a position that is easy to puncture (i.e., a vein with large blood-vessel diameter and near the body surface).

In the step S24, the blood vessel rendering function 114 of the processing circuitry 17 renders the blood vessel portions from the 3D image. First, the blood vessel rendering function 114 calculates the difference between the direction of the optical image generated by the camera 3 and the direction of the 3D image. Further, the blood vessel rendering function 114 renders the blood vessel portions in the 3D image by rotating the 3D image by the difference in such a manner that the line of sight is directed as looking down from right above the center of the 3D image (i.e., a 3D image as viewed from directly above the center is obtained). Hereinafter, the rendered 3D image of the blood vessel portion(s) is referred to as "the rendered image". At this time, the blood vessel rendering function 114 colors one or more marks indicating the recommended puncture position (s) depicted in the rendered image. The coloring of the mark(s) is performed on the basis of predetermined colors assigned according to the recommended order of recommended puncture positions, for example.

Figure 11A:
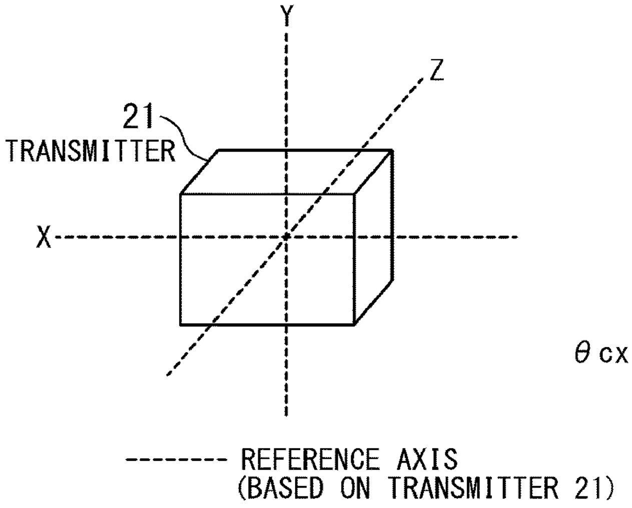
FIG. 11A is a diagram illustrating rendering and orientation alignment of a 3D image and an optical image (i.e., image generated by the camera) according to the first embodiment.
Figure 11B:
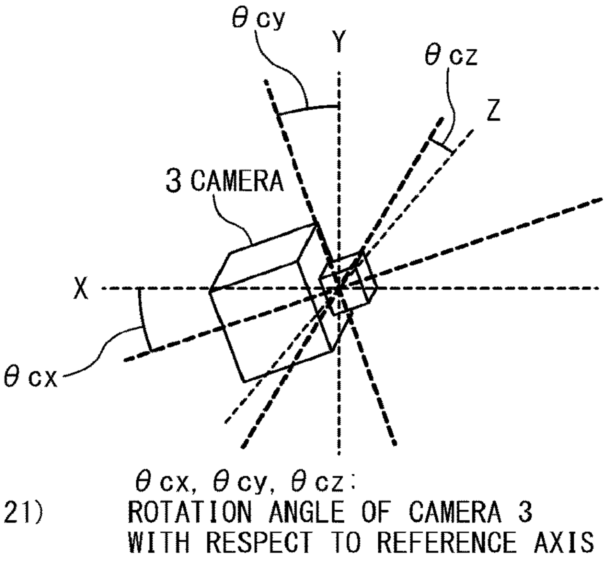
FIG. 11B is another diagram illustrating rendering and orientation alignment of a 3D image and an optical image according to the first embodiment.
Figure 11C:
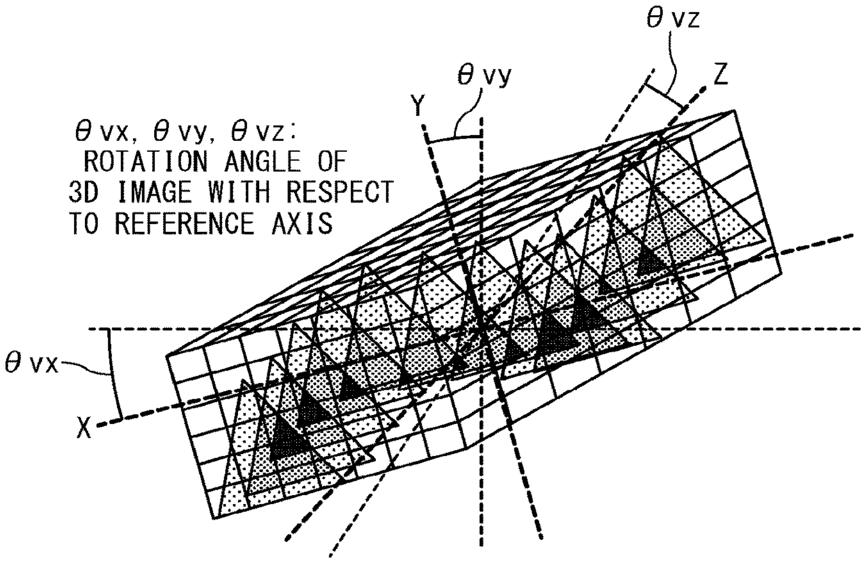
FIG. 11C is still another diagram illustrating rendering and orientation alignment of a 3D image and an optical image according to the first embodiment.

FIG. 11A to FIG. 11D illustrate rendering and orientation alignment of the 3D image and the optical image according to the first embodiment. As shown in FIG. 11A, the X-axis, Y-axis, and Z-axis, which have their origin at the center of the transmitter 21 of the magnetic sensor unit 2, are defined as the reference axes. As shown in FIG. 11B, the rotation angles of the camera 3 with respect to the respective reference axes are defined as θcx, θcy, and θcz. As shown in FIG. 11C, the rotation angles of the 3D image with respect to the respective reference axes are defined as θvx, θvy, and θvz.

Under the above-described conditions, the angle by which the 3D image is rotated so as to align with the camera 3 is calculated for each axis by Expression 2 below.

$$\theta x = \theta cx - \theta vx \qquad \text{Expression 2}$$
$$\theta y = \theta cy - \theta vy$$
$$\theta z = \theta cz - \theta vz$$

Figure 11D:
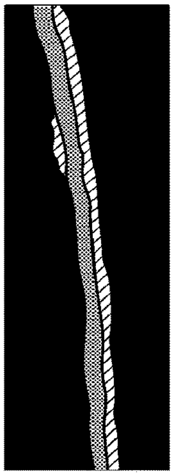
FIG. 11D is still another diagram illustrating rendering and orientation alignment of a 3D image and an optical image according to the first embodiment.

In other words, the blood vessel portion(s) in the 3D image may be rendered after rotating the viewpoint by (−θx, −θy, −θz) from directly above the 3D image. FIG. 11D illustrates the rendered image.

In the step S25, the image composition function 115 of the processing circuitry 17 composes the optical image generated by the camera 3 and the rendered image. FIG. 12A, FIG. 12B, FIG. 13A, and FIG. 13B illustrate methods for composing the optical image and the rendered image according to the first embodiment.

Figure 12A:
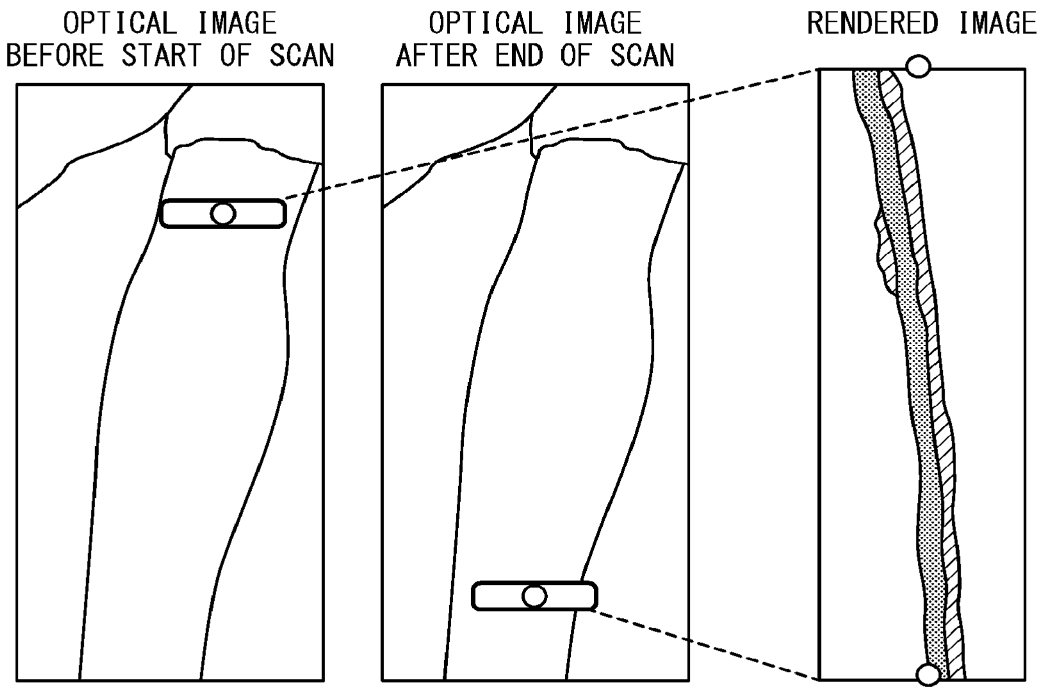
FIG. 12A is a diagram illustrating a first method of composing an optical image and a rendered image according to the first embodiment.
Figure 12B:
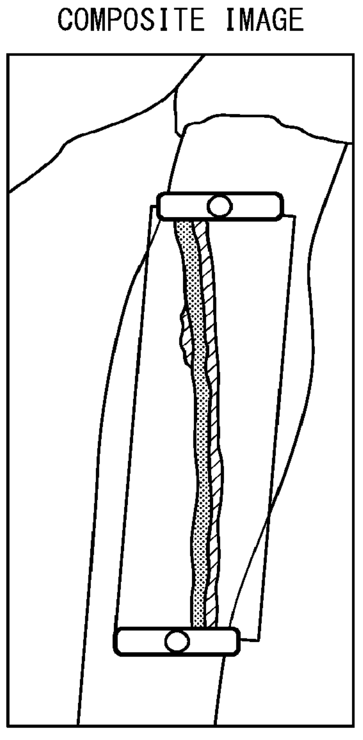
FIG. 12B is another diagram illustrating the first method of composing an optical image and a rendered image according to the first embodiment.

FIG. 12A and FIG. 12B are diagrams illustrating a first method of composing the optical image and the rendered image according to the first embodiment. The first composition method uses the position of the probe 4 depicted in the optical image. First, the image composition function 115 detects the position of the probe 4 in the optical image. For detecting the position of probe 4, a general AI (Artificial Intelligence) technique for object detection (for example, YOLO) may be used. In this case, since the object is detected as a rectangle, whether the position of the probe 4 is defined by the center or the end of the rectangle can be adjusted. As shown in FIG. 12A, both ends of the rendered image correspond to the position-s of the probe 4 before start of the scan and after completion of the scan.

Next, the image composition function 115 performs scaling and alignment of the rendered image such that both ends of the rendered image overlap the positions of the probe 4 depicted in the optical images before start of the scan and after completion of the scan. After performing the scaling and alignment, the report display function 116 displays the rendered image such that the rendered image is superimposed on the optical image, as shown in FIG. 12B.

Figure 13A:
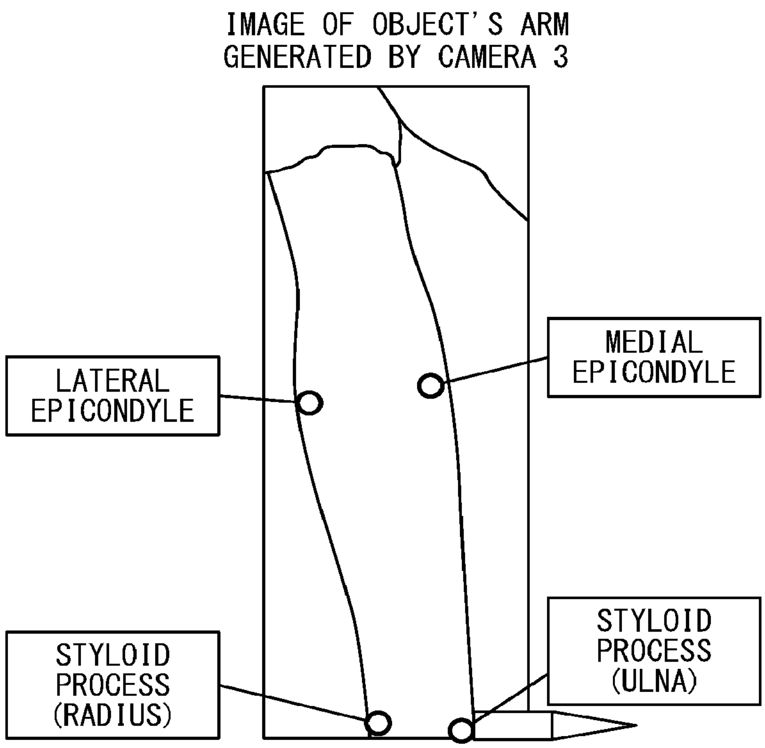
FIG. 13A is a diagram illustrating a second method of composing an optical image and a rendered image according to the first embodiment.
Figure 13B:
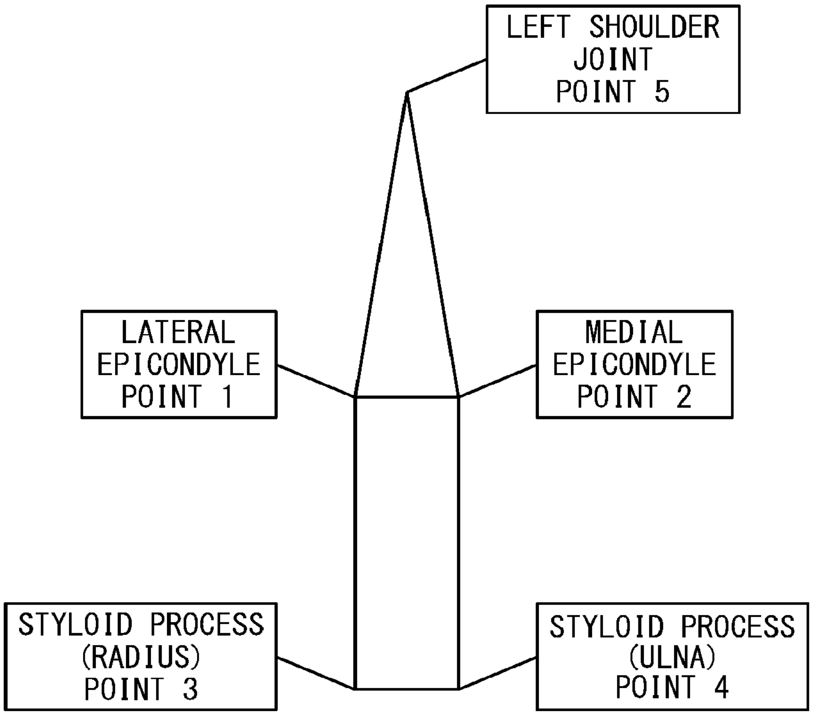
FIG. 13B is another diagram illustrating the second method of composing an optical image and a rendered image according to the first embodiment.

FIG. 13A and FIG. 13B illustrate a second method of composing the optical image and the rendered image according to the first embodiment. The second composition method uses positional information of a specific portion of the object. As shown in FIG. 13A, first, the user uses the pointing device included in the input interface 11 of the ultrasonic diagnostic apparatus 1 to specify, for example, each joint or an arbitrary portion of the arm depicted in the optical image as a specific portion. Next, the user moves the probe 4, which has the installed magnetic sensor 22, to the actual portion of the arm corresponding to the specified specific portion.

The ultrasonic diagnostic apparatus 1 obtains the latest positional information of the probe 4 from the magnetic sensor unit 2. Further, the ultrasonic diagnostic apparatus 1 associates the specific portion in the optical image with the actual positional information, and stores it in the memory 16. As a result, the positional information of the specific portion of the optical image can be specified.

After acquiring the ultrasonic images, the image composition function 115 composes the optical image and the rendered image by using the positional information of the specific portion in the optical image and the positional information of each frame image in the 3D image (i.e., positional information of each point in FIG. 13B).

In the step S26, the report display function 116 displays the composite image and a list of the recommended puncture positions on the schema report screen of the display 10. FIG. 14 illustrates the schema report screen according to the first embodiment.

The composite image is displayed on the right side of FIG. 14. Since the rendered image has at least one circular mark indicating the recommended puncture position, composing the rendered image with the optical image and displaying the resultant composite image enable showing the recommended puncture position of the object in the optical image. This processing allows the user to clearly grasp the position to be punctured in the object.

The lower left side of FIG. 14 illustrates a list of the recommended puncture positions. With respect to each of the top three recommended puncture positions with the largest determination value, a circular mark, blood-vessel diameter, vascular depth from the body surface, and distance from another blood vessel are shown in the list. This allows the user to select an easy puncturing position from the plurality of choices.

Next, details of the processing of displaying the cross-sectional images in the step S3 of FIG. 3 is described. The user operates the cursor on the composite image of the schema report screen on the display 10. The input interface 11 acquires the cursor position and outputs the cursor position to the processing circuitry 17. The MPR rendering function 117 of the processing circuitry 17 acquires the cursor position from the input interface 11. Further, the MPR rendering function 117 generates cross-sectional images of the acquired position in three orthogonal directions using the 3D image. The report display function 116 displays the generated cross-sectional images on the schema report screen.

Figure 15A:
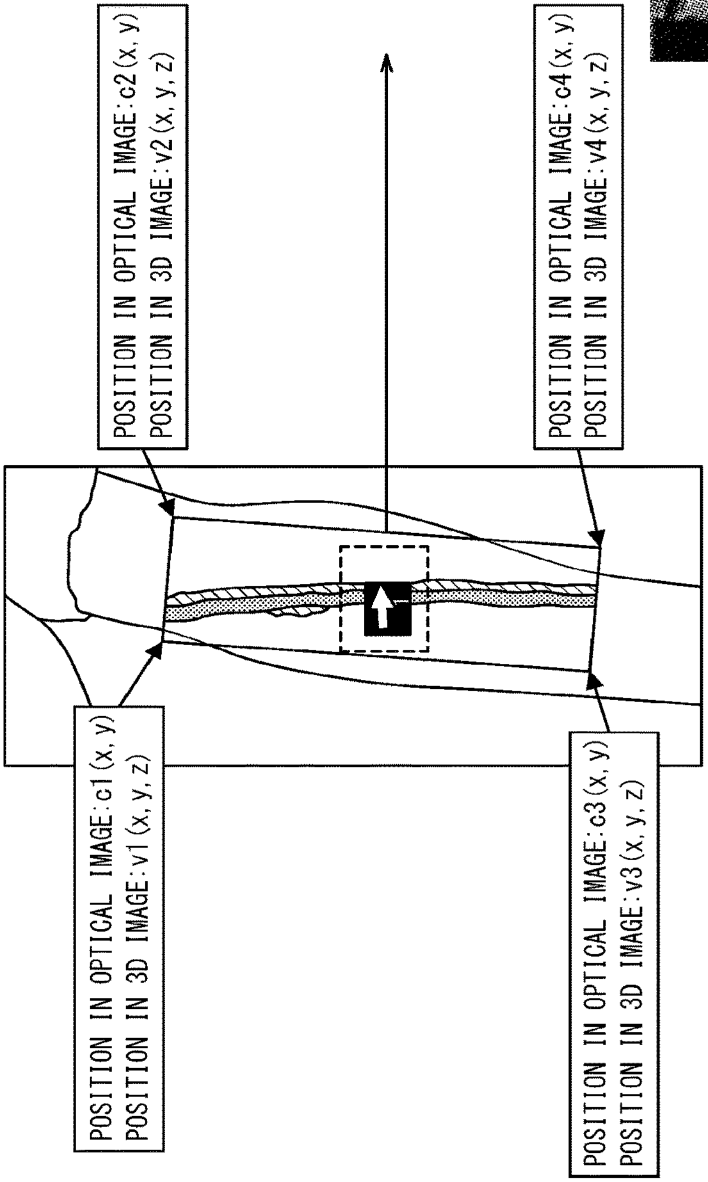
FIG. 15A is a diagram illustrating a method of displaying cross-sectional images according to the first embodiment.
Figure 15B:
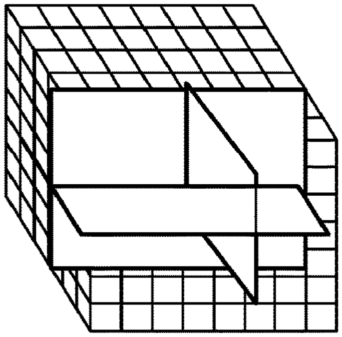
FIG. 15B is another diagram illustrating the method of displaying cross-sectional images according to the first embodiment.
Figure 15C:
FIG. 15C is still another diagram illustrating the method of displaying cross-sectional images according to the first embodiment.

FIG. 15A to FIG. 15C illustrate the method of displaying the cross-sectional images according to the first embodiment. As shown in FIG. 15A, the optical image generated by the camera 3 and the superimposed 3D image are associated or correlated based on the positional information. For example, the two-dimensional coordinates of the position c1 in the optical image correspond to the three-dimensional coordinates of the position v1 in the 3D image. Similarly, the two-dimensional coordinates of the positions c2, c3, and c4 in the optical image respectively correspond to the three-dimensional coordinates of the positions v2, v3, and v4 in the 3D image. The processing circuitry 17 can convert the two-dimensional coordinates of an arbitrary position cN in the optical image into the three-dimensional coordinates of the corresponding position vN in the 3D image on the basis of the correspondence (i.e., relationship) between the coordinates of the four positions c1 to c4 and the coordinates of the four positions v1 to v4.

Accordingly, the user designates a position in the optical image by using the input interface 11. The MPR rendering function 117 acquires the position in the optical image designated by the user from the input interface 11, and converts the acquired position into the position in the 3D image corresponding to the acquired position. Further, the MPR rendering function 117 generates the cross-sectional images of the 3D image in three orthogonal directions of the converted position. The report display function 116 displays the generated cross-sectional images on the schema report screen of the display 10. Note that image processing such as movement of the cross-sectional position in the 3D image and rotation of the cross-section can be achieved by using an appropriate image processing method similar to known 3D operations.

Second Embodiment

The second embodiment relates to a configuration in which the position and tilt angle of the camera 3 are fixed. When the position and tilt angle of the camera 3 are fixed, for example, when the relative position of the camera 3 with respect to the transmitter 21 and the rotation angle of the camera 3 with respect to the reference axis of the transmitter 21 are known in advance, there is no need to install the magnetic sensor 22 on the camera 3.

Referring to FIG. 11A to FIG. 11D, it is assumed that the rotation angles θcx, θcy, and θcz of the camera 3 with respect to the respective reference axes are fixed and known. In this case, when the rotation angles θvx, θvy, and θvz of the 3D image with respect to the respective reference axes are known, the angles θvx, θvy, and θvz, by which the 3D image should be rotated in order to align with the camera 3 in direction, can be calculated using Expression 1.

Third Embodiment

The third embodiment relates to a modification of a configuration of displaying the blood-vessel image. Although a description has been given of the configuration in which the blood-vessel image and the optical image of the arm of the object are composed and the composite image is displayed on the display 10 in the first embodiment, the configuration of superimposing the blood-vessel image on the image of the arm and displaying the superimposed image is not limited to the first embodiment and may be achieved by another embodiment.

For example, when a user wears goggles (or a head-mounted display) and looks at the arm of the object, the ultrasonic diagnostic system may display a blood-vessel image, which depicts the inside of the arm of the object and includes a mark indicating the recommended puncture position, on the goggle lenses. In this case, the field of vision of the user wearing the goggles includes the arm of the object and the blood-vessel image depicting the inside of the arm. This enables the user to check the recommended puncture position while looking at the actual arm of the object, and thus, it becomes easier for the user to perform the puncture procedure.

According to at least one embodiment as described above, information on the blood vessels of the object can be easily referred to.

While certain embodiments have been described, these embodiments have been presented by way of example only, and are not intended to limit the scope of the invention. Indeed, the novel methods and systems described herein may be embodied in a variety of other forms; furthermore, various omissions, substitutions and changes in the form of the methods and systems described herein may be made without departing from the spirit of the invention. The accompanying claims and their equivalents are intended to cover such forms or modifications as would fall within the scope and spirit of the inventions.

What is claimed is:

1. An ultrasonic diagnostic apparatus, comprising:

a camera;

a display;

an ultrasonic probe; and processing circuitry configured to acquire an appearance image depicting a body surface of an object, the appearance image being imaged by the camera, acquire an echo signal acquired by a scan of the object with the ultrasonic probe, and positional information indicating a position where the scan is performed by the ultrasonic probe to associate the echo signal and the positional information with each other, acquire a three-dimensional (3D) ultrasonic image based on the associated echo signal and the positional information, generate a composite image depicting a blood vessel of the object on the body surface of the object based on the appearance image and the 3D ultrasonic image, cause the display to display the generated composite image, color-code multiple candidates for recommended puncture positions according to a recommended order based on at least one of a blood-vessel diameter, a vascular depth from a body surface, and a distance to another blood vessel shown in the generated composite image, and cause the display to display the color-coded multiple candidates for the recommended puncture positions.

2. The ultrasonic diagnostic apparatus according to claim 1, wherein the processing circuitry is further configured to:

generate a plurality of frame images depicting an inside of the object from the echo signal;

use the 3D ultrasonic image to calculate blood vessel data that include the blood-vessel diameter, the vascular depth from the body surface, and the distance to the another blood vessel shown in the plurality of frame images; and specify the recommended puncture positions from the blood vessel shown in the plurality of frame images based on the blood vessel data.

3. The ultrasonic diagnostic apparatus according to claim 1, wherein the processing circuitry is further configured to:

extract a blood-vessel image depicting a blood vessel inside the object from the 3D ultrasonic image; and color-code the blood-vessel image depending on the blood-vessel diameter and the vascular depth from the body surface.

4. The ultrasonic diagnostic apparatus according to claim 1, wherein the processing circuitry is further configured to:

generate cross-sectional images in three orthogonal directions of an arbitrary position in the 3D ultrasonic image; and cause the display to display the generated cross-sectional images.

* * * * *